US012593961B2

(12) United States Patent
Shimizu

(10) Patent No.: US 12,593,961 B2
(45) Date of Patent: Apr. 7, 2026

(54) ENDOSCOPE SYSTEM AND SUCTION UNIT

(71) Applicant: OLYMPUS MEDICAL SYSTEMS CORP., Tokyo (JP)

(72) Inventor: Soichiro Shimizu, Kawasaki (JP)

(73) Assignee: Olympus Medical Systems Corp., Tokyo (JP)

( * ) Notice: Subject to any disclaimer, the term of this patent is extended or adjusted under 35 U.S.C. 154(b) by 433 days.

(21) Appl. No.: 18/112,240

(22) Filed: Feb. 21, 2023

(65) Prior Publication Data

US 2023/0263374 A1 Aug. 24, 2023

Related U.S. Application Data

(60) Provisional application No. 63/312,873, filed on Feb. 23, 2022.

(51) Int. Cl.
*A61B 1/00* (2006.01)
*A61B 1/005* (2006.01)
(52) U.S. Cl.
CPC ...... *A61B 1/00068* (2013.01); *A61B 1/00094* (2013.01); *A61B 1/0052* (2013.01)
(58) Field of Classification Search
CPC ............ A61B 1/00068; A61B 1/00094; A61B 1/0052
See application file for complete search history.

(56) References Cited

U.S. PATENT DOCUMENTS

| | | | |
|---|---|---|---|
| 2003/0181786 A1* | 9/2003 | Heimberger | A61B 1/00068 600/159 |
| 2006/0241348 A1* | 10/2006 | Kohno | A61B 1/00068 600/158 |
| 2007/0249904 A1 | 10/2007 | Amano et al. | |
| 2009/0216084 A1* | 8/2009 | Yamane | A61B 1/00068 600/159 |

(Continued)

FOREIGN PATENT DOCUMENTS

| | | |
|---|---|---|
| CN | 101032391 A | 9/2007 |
| CN | 102697445 A | 10/2012 |

(Continued)

OTHER PUBLICATIONS

Office Action dated Aug. 21, 2025, issued in corresponding Chinese Patent Application No. 202211423004.1.

*Primary Examiner* — Aaron B Fairchild
(74) *Attorney, Agent, or Firm* — Morgan, Lewis & Bockius LLP

(57) ABSTRACT

An endoscope system includes an endoscope and a suction unit. The endoscope includes an insertion portion configured to be inserted into a subject, an operation portion provided on a proximal end side of the insertion portion, and an angle knob provided on the operation portion for operating the bending portion; and an opening provided in the operation portion, wherein the opening is connected to a lumen provided in the endoscope. The suction unit includes a suction conduit, a protrusion inserted into the opening, and a suction button. In a side view perpendicular to an axis of (Continued)

rotation of the angle knob, a center of a top surface of the suction button, a center of the opening, and the angle knob are arranged along an imaginary straight line with the center of the opening located between the center of the top surface of the suction button and the angle knob.

19 Claims, 9 Drawing Sheets

(56)                    References Cited

U.S. PATENT DOCUMENTS

| | | | |
|---|---|---|---|
| 2013/0012780 A1 | 1/2013 | Nakamura et al. | |
| 2015/0094655 A1 | 4/2015 | Fukida et al. | |
| 2015/0216394 A1 | 8/2015 | Toyoda | |

FOREIGN PATENT DOCUMENTS

| | | | |
|---|---|---|---|
| CN | 102834041 A | 12/2012 | |
| CN | 104703530 A | 6/2015 | |
| CN | 104825116 A | 8/2015 | |
| JP | 2001-061772 A | 3/2001 | |
| JP | 2012-075746 A | 4/2012 | |
| JP | 2013-202099 A | 10/2013 | |
| JP | 2015-165842 A | 9/2015 | |

* cited by examiner

ENDOSCOPE SYSTEM AND SUCTION UNIT

RELATED APPLICATION DATA

This application is based on and claims priority under 35 U.S.C. § 119 to U.S. Provisional Application No. 63/312,873 filed on Feb. 23, 2022, the entire contents of which are incorporated herein by reference.

FIELD OF DISCLOSURE

The present disclosure relates to an endoscope system including an endoscope and a suction unit externally provided on the endoscope, and also relates to the suction unit.

BACKGROUND

In a case of bleeding inside a subject or the like in examination and medical treatment with an endoscope, blood and the like are suctioned to identify a bleeding site. However, a suction function built into a conventional endoscope has restrictions on, for example, a pipeline diameter, and suction capacity is insufficient in some cases.

Thus, for example, Japanese Patent Application Laid-Open Publication No. 2012-75746 discloses an endoscope system including a suction device having high suction force, separately from a suction function of an endoscope, the suction device being connected to an externally provided suction tube that is attached to an insertion portion.

SUMMARY OF THE DISCLOSURE

An endoscope system according to an aspect of the present disclosure includes an endoscope and a suction unit. The endoscope includes an insertion portion configured to be inserted into a subject, wherein the insertion portion includes a bending portion, an operation portion provided on a proximal end side of the insertion portion, and an angle knob provided on the operation portion for operating the bending portion; and an opening provided in the operation portion, wherein the opening is connected to a lumen provided in the endoscope. The suction unit including a suction conduit, a protrusion inserted into the opening, and a suction button. In a side view perpendicular to an axis of rotation of the angle knob, a center of a top surface of the suction button, a center of the opening, and the angle knob are arranged along an imaginary straight line with the center of the opening located between the center of the top surface of the suction button and the angle knob.

A suction unit according to an aspect of the present disclosure includes a suction button movable along a first axis; and an endoscope insertable protrusion extending along a second axis. The second axis is tilted relative to the first axis.

DETAILED DESCRIPTION

A configuration according to an aspect of the present disclosure will be described below. Note that, in description below, diagrams based on the embodiment are schematic, and a relation between thickness and width of each part, a thickness ratio of each part, and the like are different from reality. Furthermore, a dimensional relation, a ratio, or the like is different between parts of drawings in some cases.

In a typical endoscope system including an externally provided suction device as in conventional cases, a button unit for operating the suction device is mounted on an operation portion of an endoscope.

However, the conventional button unit has such a problem that it is difficult for a user to perform a suction operation by using the externally provided suction device while operating an angle knob of the endoscope with a single hand to bend a bending portion. In other words, the conventional button unit has such a problem that it is difficult for the user to reach a suction button with, for example, a forefinger or a middle finger while operating the angle knob.

Thus, the user operates the conventional button unit with both hands when simultaneously performing an operation of the angle knob and an operation of the suction button. Note that the user can use a single hand to operate the suction button with, for example, a ring finger or a little finger simultaneously with an operation of the angle knob, but an amount of force on a button pressing operation, correctness, and the like decrease.

Furthermore, the conventional button unit is fixed on the operation portion of the endoscope in a sandwiching manner. Thus, the button unit is easily displaced due to rotation or the like during a procedure with the endoscope, which has been another problem.

Thus, the present disclosure is intended to provide an endoscope system and a suction unit that have improved operability when a user operates, with a single hand, a suction device different from a suction function provided to an endoscope.

Figure 1:
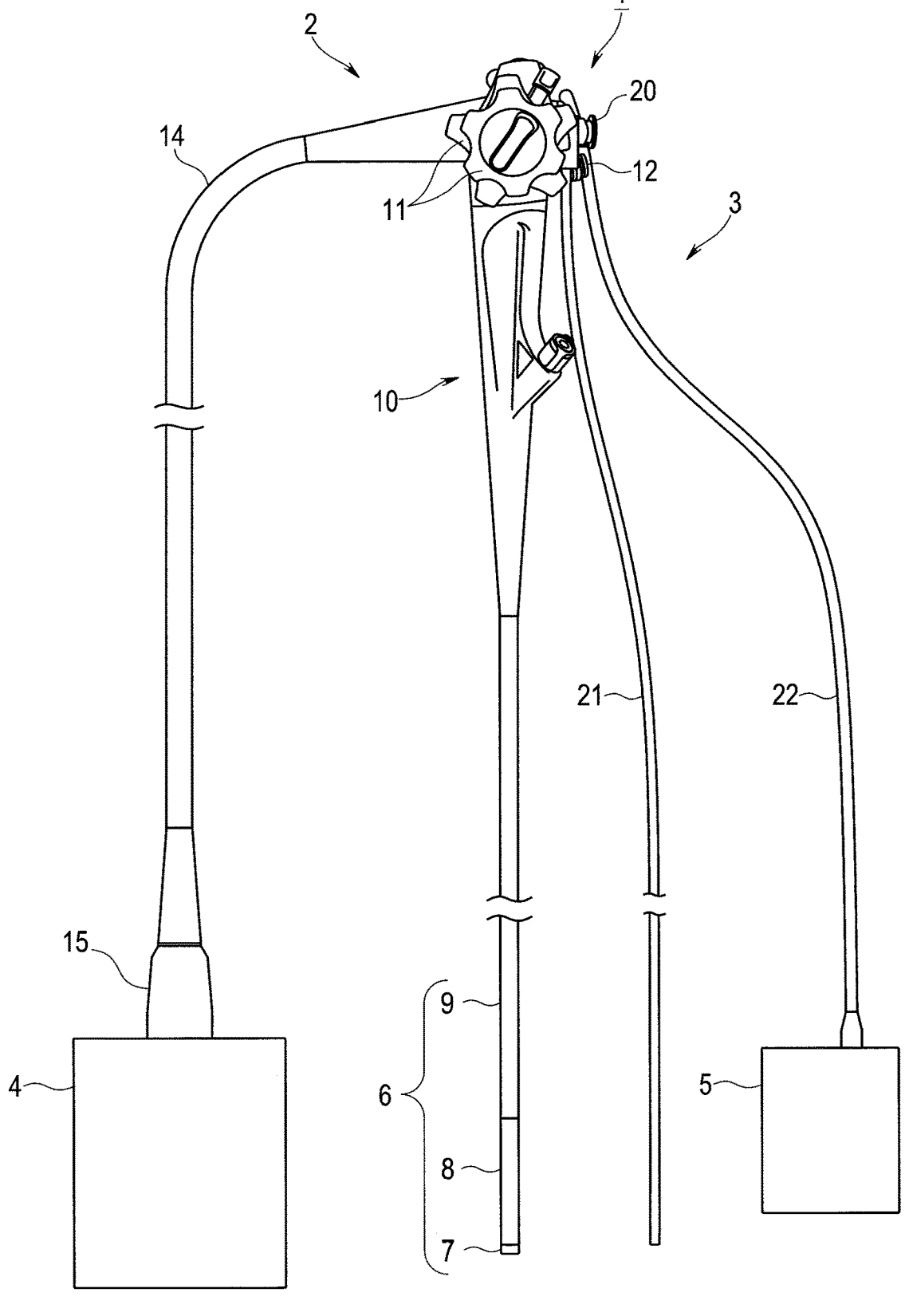
FIG. 1 is a diagram schematically illustrating an endoscope system according to an aspect of the present disclosure.

An endoscope system 1 according to the present embodiment will be described below. As illustrated in FIG. 1, the endoscope system 1 includes an endoscope 2, a suction unit 3, a video processor 4 of a camera control unit (CCU), and a suction device 5. The endoscope system 1 has a configuration in which not a suction function built into the endoscope 2 but the suction unit 3 externally provided and having strong suction force is mounted on the endoscope 2.

First, a schematic configuration of the endoscope 2 according to the present embodiment will be described below. The endoscope 2 includes an insertion portion 6, an operation portion 10, and a universal code 14.

The insertion portion 6 is an elongated member that can be inserted into a subject. The insertion portion 6 includes a distal end portion 7, a bending portion 8, and a flexible tube portion 9. The operation portion 10 is provided on a proximal end side of the insertion portion 6.

The distal end portion 7 is disposed at a distal end of the insertion portion 6. The bending portion 8 is disposed on a proximal end side of the distal end portion 7. The bending portion 8 is an active bending site and is freely bendable. The flexible tube portion 9 has flexibility and is disposed on a proximal end side of the bending portion 8. The flexible tube portion 9 is a passive flexible site and is connected to a distal end side of the operation portion 10.

The distal end portion 7 is provided with an observation window (not illustrated). Photographing light incoming through the observation window is photoelectrically converted by an image sensor (not illustrated) built into the distal end portion 7. An image pickup cable extending from the image sensor is also inserted in the insertion portion 6, the operation portion 10, and the universal code 14 and extended to an endoscope connector 15.

The operation portion 10 is provided with a pair of angle knobs 11 for operating bending of the bending portion 8. The operation portion 10 is provided with, for example, a plurality of video switches for operating freeze of an endoscope image, release of image pickup, and the like, and a plurality of buttons for operating endoscope functions. Note that the plurality of buttons includes a gas-liquid feeding button (first button) 12 of a control switch for operating gas-liquid feeding. The angle knob 11 is provided on the operation portion 10 for operating the bending portion 8. The operation portion 10 extends in a longitudinal direction with operation portion 10 at a first longitudinal end. The axis of rotation of the angle knob 11 is perpendicular to the longitudinal direction, and the side view is perpendicular to the longitudinal direction. The operation portion 10 includes the first button 12 and a second button 18 or 19 arranged in the longitudinal direction. In the side view, the first button 12 is on a first side of the imaginary straight line and the second button 18 or 19 is on a second side of the imaginary straight line.

The universal code 14 is a composite cable extending from a side part of the operation portion 10. The endoscope connector 15 is provided at an extension end of the universal code 14. The endoscope connector 15 is connected to the video processor 4 of the camera control unit (CCU) including a light source device.

A light source is built into the video processor 4. Light from the light source is transmitted to a non-illustrated light guide bundle inserted in the universal code 14, the operation portion 10, and the insertion portion 6.

Light emitted from the video processor 4 becomes illumination light that is emitted to a subject through an illumination window (not illustrated) provided to the distal end portion 7 of the insertion portion 6. Note that, in the endoscope 2, a light source such as an LED may be built in as an illumination apparatus in the distal end portion 7.

The endoscope 2 configured as described above is a single-use disposable product that is discarded after use (used once) but may be a reuse product that is sterilized and reused.

Subsequently, a schematic configuration of the suction unit 3 according to the present embodiment will be described below. The suction unit 3 is externally provided to the endoscope 2. The suction unit 3 includes a suction button unit 20, a first suction tube 21 that is inserted into a subject, and a second suction tube 22 that is disposed outside. Note that the suction unit 3 has a configuration in which the suction button unit 20 for performing an operation to turn on and off suction can be mounted on and dismounted from the operation portion 10 of the endoscope 2.

The first suction tube 21 is, for example, a living-body-compatible silicone tube for insertion into a subject. The first suction tube 21 is connected to the suction button unit 20. At installation, the first suction tube 21 is helically wound around the insertion portion 6 of the endoscope 2 or fixed to the insertion portion 6 by a band or the like.

The second suction tube 22 is, for example, a silicone or rubber tube that is disposed outside a subject. One end of the second suction tube 22 is connected to the suction button unit 20. The other end of the second suction tube 22 is connected to the suction device 5 as an external instrument.

The suction device 5 includes a suction pump and a liquid discharge tank (not illustrated). In use, the suction device 5 may be always driven.

Figure 2:
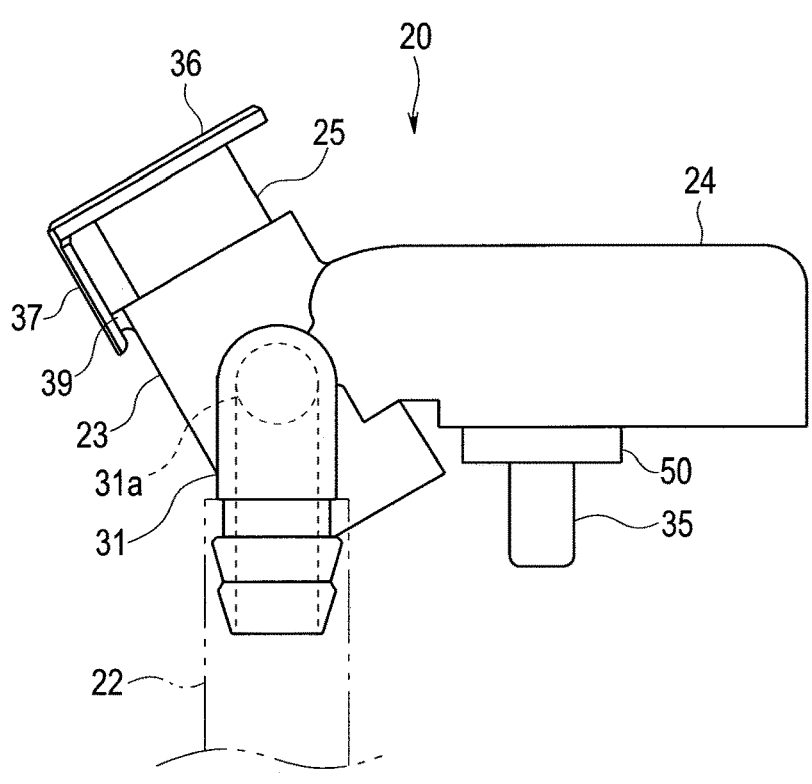
FIG. 2 is a side view illustrating a configuration of a suction button unit.

Subsequently, a schematic configuration of the suction button unit 20 according to the present embodiment will be described below. The suction button unit 20 is formed of metal or resin. As illustrated in FIG. 2, the suction button unit 20 includes a syringe member 23, a pipeline member 24, and a piston member 25. The body member includes one or more of the pipeline member 24 and the connection pipe 34. The suction unit 3 includes a suction conduit, a protrusion 35 inserted into the opening, and a suction button 23. In a side view perpendicular to an axis of rotation of the angle knob 11, a center of a top surface 36 of the suction button 23, a center of the opening, and the angle knob are arranged along an imaginary straight line with the center of the opening located between the center of the top surface of the suction button and the angle knob. In a direction perpendicular to the longitudinal direction, the center of the top surface 36 of the suction button 23 is at a first distance from the protrusion 35. Relative to the longitudinal direction, the suction button 23 is on an opposite side of the operation portion 10 from the angle knob 11. The first button 12 may be disposed closer to the insertion portion 6 than the suction button 23.

The syringe member 23 is a bottomed tubular body. A tube joint 31 is extended from a side periphery of the syringe member 23. The tube joint 31 includes a flow path 31a as an internal pipeline communicating with inside of the syringe member 23. The second suction tube 22 is connected to the tube joint 31.

Figure 3:
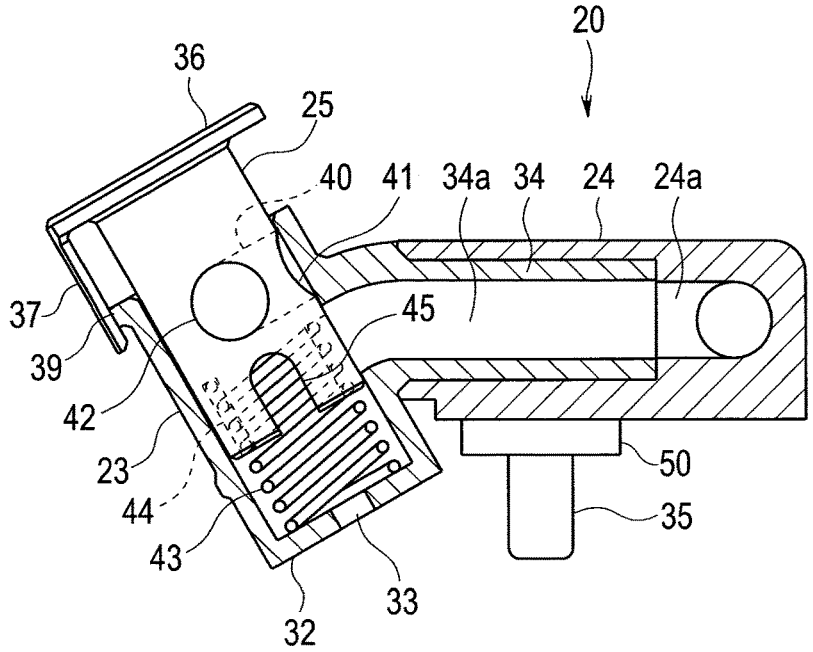
FIG. 3 is a cross-sectional view illustrating the configuration of the suction button unit.
Figure 5:
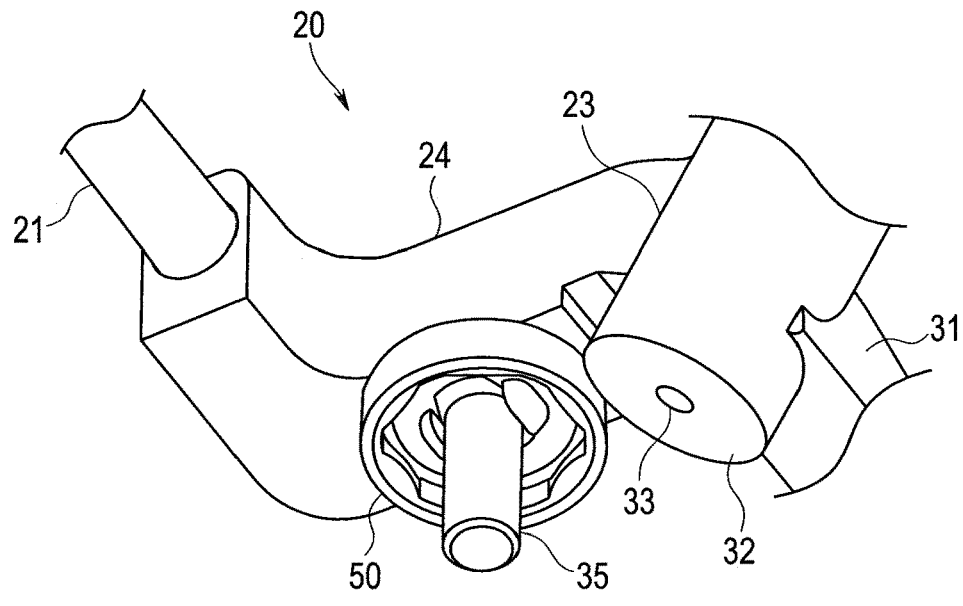
FIG. 5 is a perspective view illustrating a back surface side of the configuration of the suction button unit.

As illustrated in FIG. 3, a hole vent 33 is formed at a bottom part 32 of the syringe member 23 (refer to FIG. 5). A connection pipe 34 extends from a side periphery of the syringe member 23 at a predetermined angle.

The connection pipe 34 includes a flow path 34a as an internal pipeline communicating with inside of the syringe member 23. The connection pipe 34 is fitted and connected to the pipeline member 24 in an airtight (watertight) manner. The flow path 34a of the connection pipe 34 communicates with a flow path 24a of the pipeline member 24.

Note that the syringe member 23 is connected such that a longitudinal axial direction of the syringe member 23 is tilted at a predetermined angle relative to a transverse axial direction of the pipeline member 24.

The pipeline member 24 is an L-shaped block body in which the flow path 24a is formed. The connection member 24 is connected to the first suction tube 21. A fixation portion (protrusion) 35 as a connection rod body extends from one surface of the pipeline member 24. The fixation portion 35 extends in a transverse direction of the pipeline member 24.

An attachment rubber 50 as a circular-disk fixation member is provided on the one surface of the pipeline member 24. The attachment rubber 50 into which the fixation portion 35 is inserted is fixed to the one surface of the pipeline member 24.

The piston member 25 can be a column-shaped body. The piston member 25 is provided to the syringe member 23 in a freely protruding and retracting manner. The piston member 25 includes a button top (top surface) 36 of a suction button.

Figure 4:
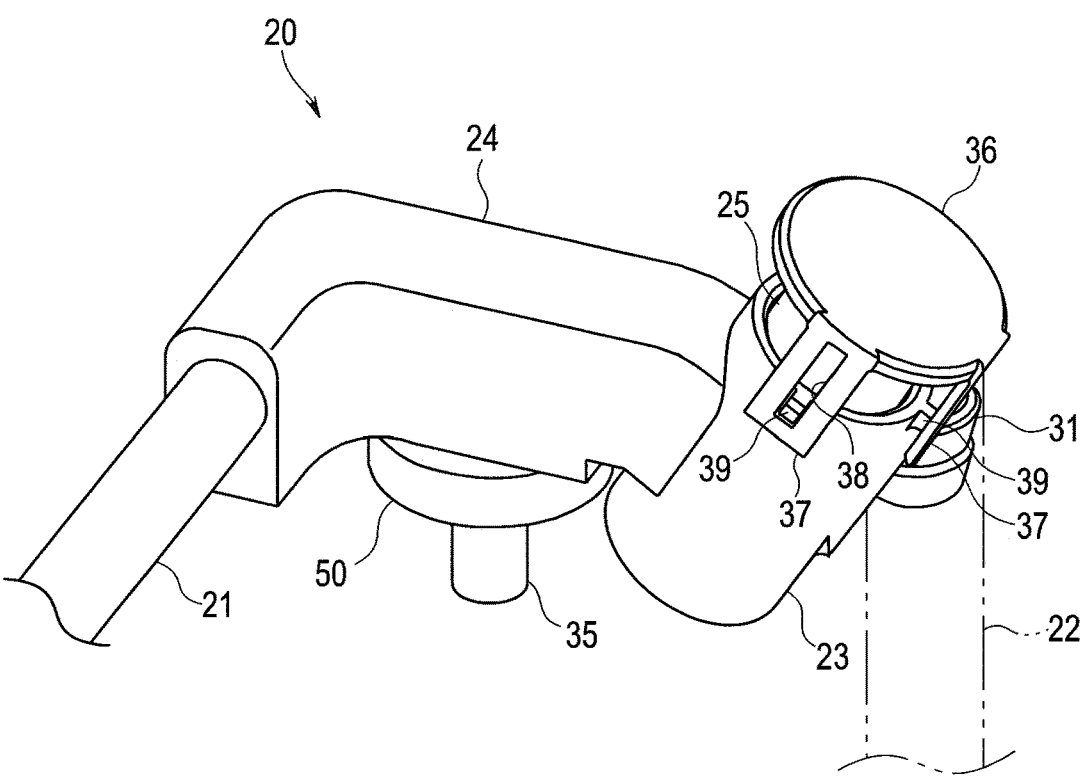
FIG. 4 is a perspective view illustrating the configuration of the suction button unit.

The button top 36 has a circular-disk flange shape and is provided with rectangular plate guides 37 at two places on a side periphery (refer to FIG. 4). The two guides 37 are extended from an outer surface of the syringe member 23 with a predetermined gap therebetween. A shortest distance from a surface of the operation portion 10 to the top surface 36 of the suction button 23 defines a first height. The operation portion 10 includes a button 12, 18 or 19 a shortest distance from the surface of operation portion 10 to a top surface of the button 12 12, 18 or 19 defines a second height. The second height is smaller than the first height.

Each guide 37 may have a rectangular hole 38. A click portion 39 as a convex portion provided on an outer periphery portion of the syringe member 23 is fitted into the long hole 38. The guide 37 is linearly guided along the long hole 38 by the click portion 39. Accordingly, sliding of the piston member 25 relative to the syringe member 23 is linearly guided.

Note that the click portion 39 locks the guide 37 and prevents the piston member 25 from coming off the syringe member 23. In addition, the two guides 37 restrict rotation of the piston member 25 about a longitudinal axis.

The piston member 25 includes a flow path (first suction channel) 40 as an internal pipeline. The flow path 40 may be formed in a L shape in a sectional direction orthogonal to the longitudinal axis of the piston member 25.

Openings 41 and 42 of the flow path 40 are formed through a side peripheral surface of the piston member 25. The two openings 41 and 42 may be formed at different outer periphery positions separated from each other by 90° in a section orthogonal to the longitudinal axis of the piston member 25. The button 20 includes the first suction channel 40. And the suction tube 22 having a second suction channel in fluid communication with the first suction channel 40. The body member has the third suction channel 34a in fluid communication with the first suction channel 40. The suction button 23 extends from a first surface of the body member. The endoscope insertable protrusion 35 extends from a second surface of the body member. The first surface is on an opposite side of the body member from the second surface. The suction button 23 is switchable between a first state and a second state. In the first state, fluid flow between the first suction channel 40 and the third suction channel 34a is prevented, and in the second state, fluid flow between the first suction channel 40 and the third suction channel 34a is allowed.

A coil spring 43 as an urging member is provided inside the syringe member 23. The piston member 25 is urged in a direction protruding from the syringe member 23 by the coil spring 43. In an absence of an applied external force, the suction button 23 is biased to be in the first state.

Note that a circumferential groove 44 in which part of the coil spring 43 is positioned is formed on the piston member

6

25. In addition, a cutout 45 communicating with the circumferential groove 44 is formed at part of an outer periphery of the piston member 25.

The cutout 45 is formed at a position where the cutout 45 communicates with the flow path 31a of the tube joint 31 in a state in which the piston member 25 protrudes from the syringe member 23.

The suction button unit 20 configured as described above switches between a suction state and a non-suction state in accordance with protrusion and retraction of the piston member 25.

In the suction state of the suction button unit 20, the piston member 25 is pressed into the syringe member 23 against urging force of the coil spring 43. Accordingly, the suction button unit 20 is in a suction operation state in which the piston member 25 is pressed in by a user.

More specifically, as the piston member 25 is pressed into the syringe member 23, the openings 41 and 42 of the flow path 40 move to positions of the flow path 34a of the pipeline member 24 and the flow path 31a of the tube joint 31.

Thus, the three flow paths 31a, 34a, and 40 communicate with one another in the suction button unit 20. Accordingly, the first suction tube 21 and the second suction tube 22 communicate with each other.

As a result, negative pressure occurs inside the first suction tube 21, the flow paths 31a, 34a, and 40 of the suction button unit, and the second suction tube 22 by suction drive of the suction device 5, and the suction unit 3 switches to the suction state.

In the non-suction state of the suction button unit 20, the piston member 25 is pressed by urging force of the coil spring 43 in the direction protruding from the syringe member 23. Accordingly, the suction button unit 20 is in a non-suction operation state in which the piston member 25 is not pressed in by the user.

The piston member 25 is pressed until the openings 41 and 42 of the flow path 40 reach positions different from the positions of the flow path 34a of the pipeline member 24 and the flow path 31a of the tube joint 31.

In this state, the flow paths 31a and 34a are blocked by an outer peripheral surface of the piston member 25. In other words, the suction button unit 20 is in a state in which the three flow paths 31a, 34a, and 40 do not communicate with one another. Accordingly, the first suction tube 21 and the second suction tube 22 do not communicate with each other.

As a result, the suction unit 3 switches to the non-suction state in which no negative pressure occurs inside the first suction tube 21, the flow paths 31a, 34a, and 40 of the suction button unit, and the second suction tube 22 irrespective of suction drive of the suction device 5.

Note that, in the suction unit 3, the vent 33 of the bottom part 32 of the syringe member 23 is formed so that negative pressure due to air intake by the suction device 5 does not occur inside the syringe member 23. In other words, the flow path 31a of the tube joint 31 and the cutout 45 of the piston member 25 communicate with each other in the suction button unit 20 so that external air taken into the syringe member 23 through the vent 33 is suctioned by the suction device 5.

The suction unit 3 thus configured is a single-use disposable product that is discarded after use (used once). The first suction tube 21 and the second suction tube 22 may be disposable products, and the suction button unit 20 may be a reuse product that is disassembled, sterilized, and reused.

Figure 6:
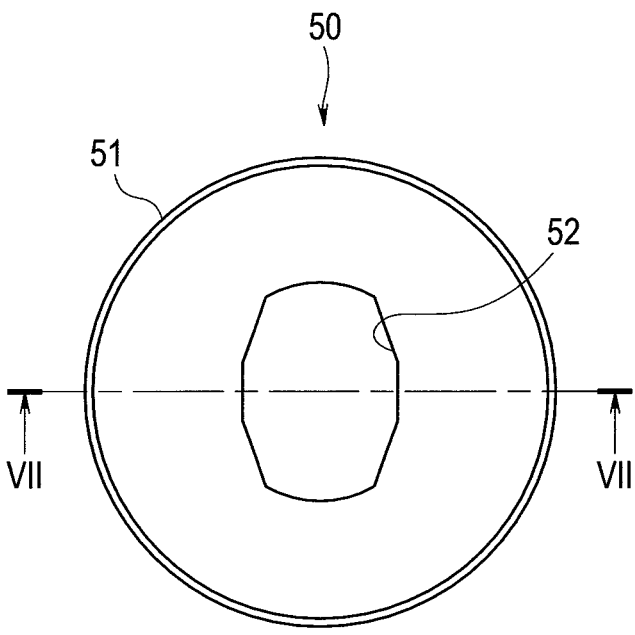
FIG. 6 is a plan view illustrating a configuration of an attachment rubber.
Figure 7:
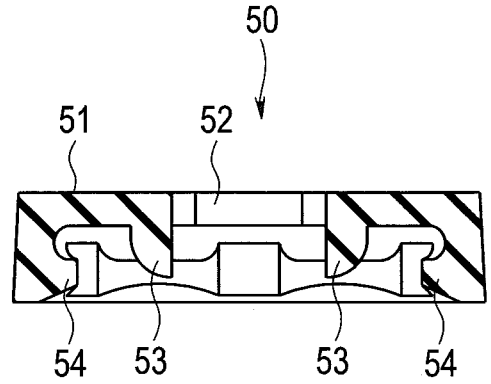
FIG. 7 is a cross-sectional view illustrating the configuration of the attachment rubber along line VII-VII in FIG. 6.
Figure 8:
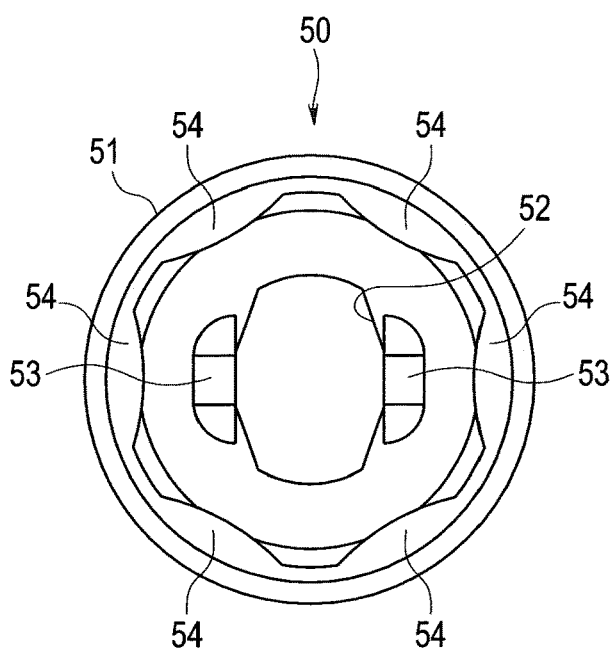
FIG. 8 is a back view illustrating the configuration of the attachment rubber.

A schematic configuration of the attachment rubber 50 according to the present embodiment will be described below. As illustrated in FIGS. 6 to 8, the attachment rubber 50 includes a body 51 formed of an elastic member such as rubber and having a hat sectional shape.

A hole 52 is formed at a center of the body 51. The fixation portion 35 of the pipeline member 24 is inserted into the hole 52.

Two convex portions 53 as engagement portions and a plurality of, six in the present example, ribs 54 are formed on a back surface side of the body 51. The two convex portions 53 are formed as protrusions opposed to each other across the hole 52. The six ribs 54 protrude in a direction toward a center of the body 51. The suction unit 3 includes the engagement portion 53 provided around the protrusion 35 and configured to contact the opening 13. The engagement portion 53 prevents the suction unit 3 from rotating relative to the operation portion 10. The suction unit 3 is connectable to a medical device by insertion of the endoscope insertable protrusion 35 into an opening 13 of the medical device 2. When the endoscope insertable protrusion 35 is inserted into the opening 13, the suction unit 3 is prevented from moving relative to the medical device 2. The surface of the endoscope insertable protrusion 35 includes a rib 54. When the endoscope insertable protrusion 35 is inserted into the opening 13, the rib 54 prevents the endoscope insertable protrusion 35 from being removed from the opening 13.

The body 51 of the attachment rubber 50 may be firmly fixed to the one surface of the pipeline member 24 (bottom surface) of the suction button unit 20 by fixing, bonding or welding.

Figure 9:
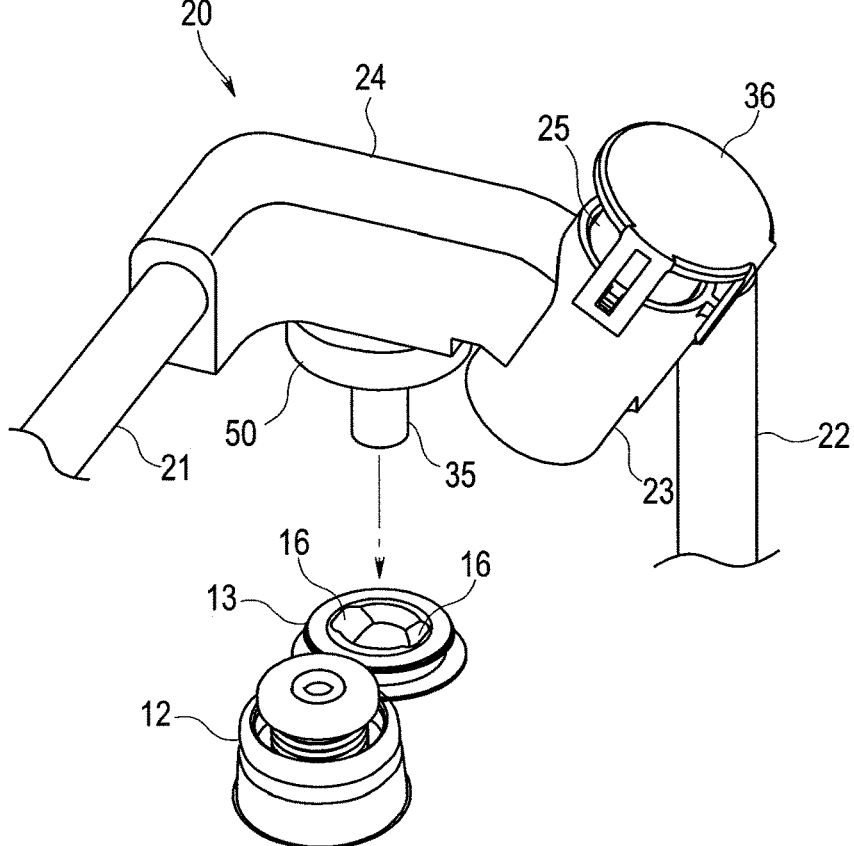
FIG. 9 is a perspective view schematically illustrating a state in which the suction button unit is mounted on a suction cylinder of an operation portion.

The suction unit 3 is mounted on the operation portion 10 of the endoscope 2. In this case, as illustrated in FIG. 9, the fixation portion 35 of the pipeline member 24 of the suction button unit 20 is inserted into a suction cylinder (opening) 13 of the operation portion 10. Then, the attachment rubber 50 engages with the suction cylinder 13 in an airtight (watertight) manner. Note that the suction cylinder 13 is provided adjacent to the gas-liquid feeding button 12 on one surface of the operation portion 10. The opening 13 is provided in the operation portion 10. The opening 13 is connected to a lumen provided in the endoscope 2

Figure 10:
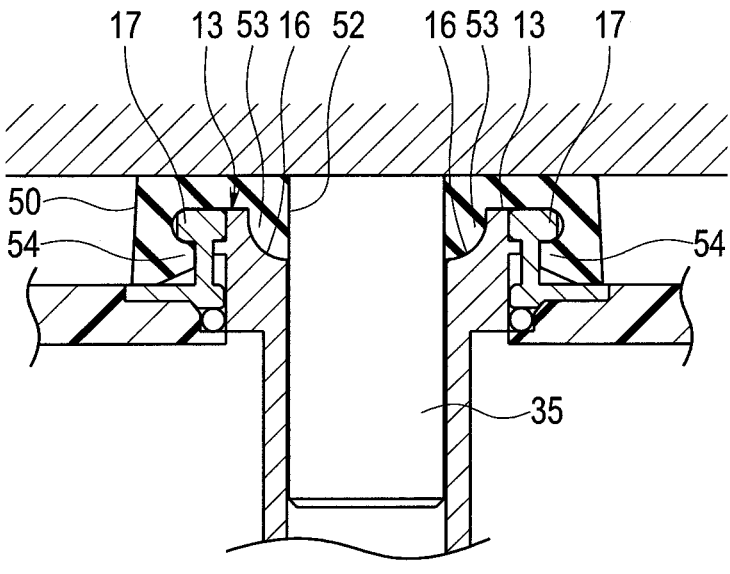
FIG. 10 is a cross-sectional view illustrating a state in which the attachment rubber engages with the suction cylinder.

In this case, as illustrated in FIG. 10, the two convex portions 53 of the attachment rubber 50 engage with two concave portions 16 as engagement counterpart portions provided to the suction cylinder 13. The six ribs 54 of the attachment rubber 50 lock an outward flange 17 of the suction cylinder 13.

In this state, the suction button unit 20 is prevented from rotating since the two convex portions 53 of the attachment rubber 50 engage with the two concave portions 16 of the suction cylinder 13, respectively. Moreover, the suction button unit 20 is prevented from falling since the six ribs 54 of the attachment rubber 50 lock the outward flange 17 of the suction cylinder 13.

In this manner, the suction button unit 20 is prevented from falling and rotating by the attachment rubber 50 when mounted on the suction cylinder 13. Note that concave and convex shapes for engagement of the two convex portions 53 of the attachment rubber 50 and the two concave portions 16 of the suction cylinder 13 as a prevention structure of rotation of the suction button unit 20 may be interchanged.

Subsequently, a state in which the suction button unit 20 of the suction unit 3 is mounted on the operation portion 10 of the endoscope 2 will be described below.

Figure 11:
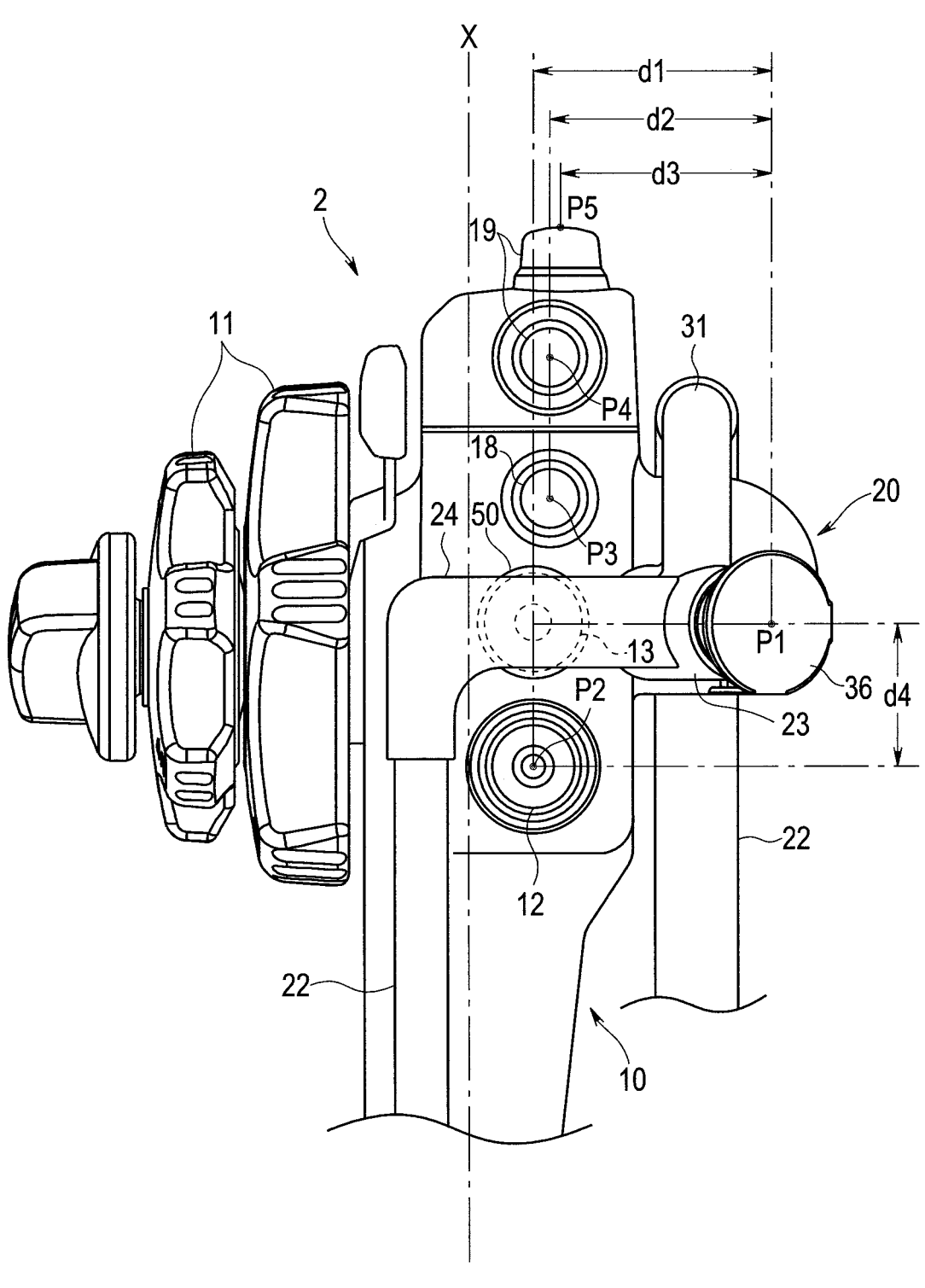
FIG. 11 is a front view illustrating the operation portion on which the suction button unit is mounted.

As illustrated in FIG. 11, a top surface center P1 of the button top 36 of the suction button unit 20 is disposed at a predetermined distance d1 from a top surface center P2 of the gas-liquid feeding button 12 in a direction orthogonal to a longitudinal axis X of the operation portion 10 and departing from the pair of angle knobs 11.

The top surface center P1 of the button top 36 of the suction button unit 20 is separated from top surface centers P3, P4, and P5 of a plurality of video switches (second buttons) 18 and 19 by predetermined distances d2 and d3 in the direction orthogonal to the longitudinal axis X of the operation portion 10 and departing from the pair of angle knobs 11.

In other words, in a state in which the suction button unit 20 is connected to the suction cylinder 13 of the operation portion 10, the button top 36 is disposed at a position further separated from the suction cylinder 13 on a side opposite the angle knobs 11 with respect to a central axis (the longitudinal axis X) in a longitudinal direction of the operation portion 10 than other operation switches such as the gas-liquid feeding button 12 and the plurality of video switches 18 and 19. In other words, the button top 36 of the suction button is disposed at a position separated from the suction cylinder 13 by a predetermined distance with the angle knobs 11 at an origin.

Note that the button top 36 is disposed at a position at least separated on the side opposite the angle knobs 11 with respect to a line connecting the gas-liquid feeding button 12 and the suction cylinder 13. In the present example, the button top 36 is disposed on a side of the suction cylinder 13 in a direction intersect or orthogonal to the longitudinal axis X of the operation portion 10.

Accordingly, the endoscope system 1 has a configuration with which the button top 36 of the suction button unit 20 can be easily operated.

Moreover, the button top 36 is disposed such that the top surface center P1 is at a position separated by a predetermined distance d4 on a proximal end side of the top surface center P2 of the gas-liquid feeding button 12 in a direction along the longitudinal axis X of the operation portion 10. In other words, the button top 36 is disposed on a hand side of the gas-liquid feeding button 12, the hand side being opposite to a side of the operation portion 10 on which the insertion portion 6 is connected.

Note that the button top 36 is disposed between the gas-liquid feeding button 12 and the video switch 18 in a direction along the longitudinal axis X of the operation portion 10.

Accordingly, the endoscope system 1 has a configuration with which the button top 36 of the suction button unit 20 does not interfere when the angle knobs 11 are operated by fingers of a user hand grasping the operation portion 10.

Figure 12:
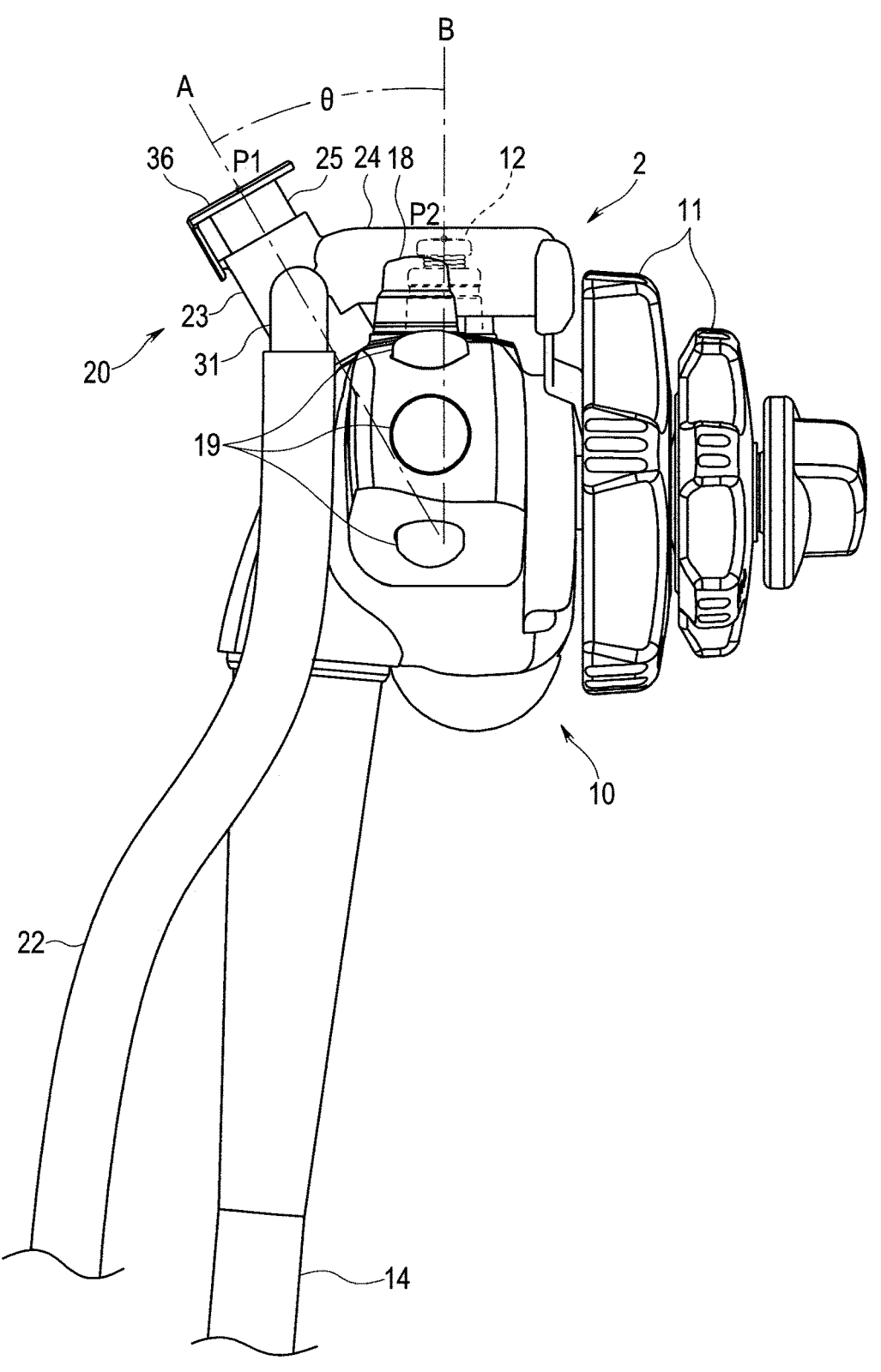
FIG. 12 is a top view illustrating the operation portion on which the suction button unit is mounted.

As illustrated in FIG. 12, the piston member 25 of the suction button unit 20 slides in an axial direction A. The gas-liquid feeding button 12 slides in an axial direction B when pressed. The axial direction A tilts relative to the axial direction B at a tilting angle θ on a side opposite a side on which the angle knobs 11 are disposed. Note that a tilt angle as the tilting angle θ is set to be, for example, equal to or smaller than 60° (60≤θ). Thus, the suction button unit 20 can be easily operated since an operation direction of the piston member 25 has the tilting angle θ (equal to or smaller than 60°) relative to an operation direction of the gas-liquid feeding button 12 in the manner described above.

Note that, in the present example, the axial direction B in which the gas-liquid feeding button 12 slides when pressed is a direction along a longitudinal axis of the fixation portion 35 inserted into the suction cylinder 13. In other words, the axial direction A in which the piston member 25 slides relative to the syringe member 23 in the suction button unit 20 tilts relative to the longitudinal axis of the fixation portion 35 at the tilting angle θ (for example, equal to or smaller than 60°) on the side opposite the side on which the angle knobs 11 are disposed. The suction button 23 is movable, for example, when a pressing operation is performed in the first axis direction A (along a first axis A), and the operation portion 10 includes the first button 12 movable, for example, when a pressing operation is performed in the second axis direction B (along a second axis B). The first axis direction A is oriented at the tilting angle θ relative to the second axis B. The tilting angle θ may be equal to or less than 60.

Figure 13:
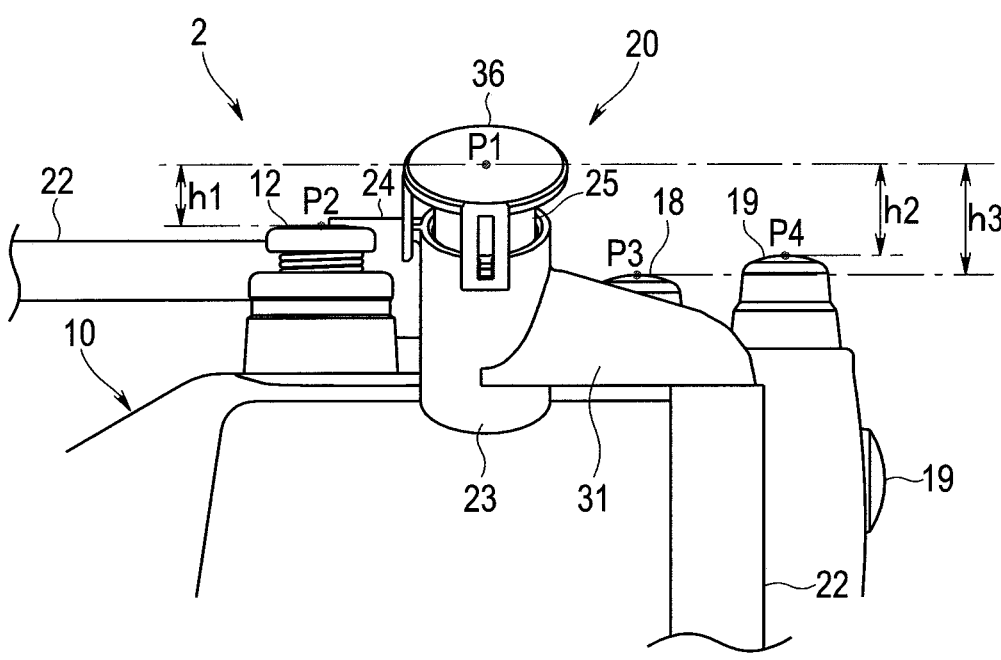
FIG. 13 is a side view illustrating part of the operation portion on which the suction button unit is mounted.

Moreover, as illustrated in FIG. 13, the suction button unit 20 is disposed such that the top surface center P1 of the button top 36 when not operated protrudes from a top surface of the operation portion 10 at a predetermined height h1 with respect to the top surface center P2 of the gas-liquid feeding button 12 when not operated. Note that the button top 36 is disposed such that the top surface center P1 when not operated protrudes from the top surface of the operation portion 10 at predetermined heights h2 and h3 with respect to the top surface centers P3 and P4 of the two video switches 18 and 19 when not operated.

In other words, the suction button unit 20 is disposed such that the button top 36 further protrudes from the top surface of the operation portion 10 than the gas-liquid feeding button 12 and the two video switches 18 and 19. Accordingly, a position of the button top 36 as an operation button of the suction unit 3 can be easily recognized.

When the suction button unit 20 of the suction unit 3 is mounted on the endoscope 2 in use of the endoscope system 1, the operation portion 10 of the endoscope 2 is usually grasped by a left hand of a user.

When operating the angle knobs 11, the user accesses the angle knobs 11 with, for example, a forefinger or a middle finger through a side of the gas-liquid feeding button 12. The suction button unit 20 according to the present embodiment is connected to the suction cylinder 13 of the operation portion 10 not to interfere with an angle operation. Moreover, the button top 36 is disposed on the hand side of the gas-liquid feeding button 12. Accordingly, the user can easily reach and access the angle knobs 11 from below the gas-liquid feeding button 12 with, for example, a forefinger or a middle finger of a hand grasping the operation portion 10.

The user can simultaneously perform a rotation operation of the angle knobs 11 and a pressing operation of the button top 36 of the suction button unit 20 with a single hand. In other words, when mounted on the operation portion 10, the suction button unit 20 does not restrict an operation of the angle knobs 11 by the user because of the above-described disposition of the button top 36.

For example, the user can operate the two angle knobs 11 with a thumb and the middle finger grasping the operation portion 10 and perform a pressing operation of the button top 36 of the suction button unit 20 with the forefinger. Thus, the user can perform a suction operation without decrease of an amount of operation force by which the button top 36 is pressed, correctness, and the like.

Note that the first suction tube 21 on the insertion portion 6 side is disposed away from the operation portion 10 so that the first suction tube 21 does not to restrict motion of fingers of the user. Accordingly, the fingers of the user can pass below the first suction tube 21. In addition, the second suction tube 22 on the suction device side is disposed along the universal code 14 so that the second suction tube 22 is unlikely to interfere with various operations of the endoscope 2.

The present disclosure is not limited to the above-described embodiment but may be modified as appropriate without inconsistency with the gist and idea of the disclosure, which can be understood from the claims, the entire specification, and the drawings.

Example 1. An endoscope system comprising:
an endoscope including
an insertion portion that is positioned on a distal end side and inserted into a subject,
an operation portion continuously provided on a proximal end side of the insertion portion,
an angle knob for operating a bending portion of the insertion portion, and
a suction cylinder provided at the operation portion; and
a suction unit including
a suction button unit mounted on the suction cylinder, and
a suction button provided at the suction button unit,
wherein the suction button is disposed at a position separated from the suction cylinder by a predetermined distance with the angle knob at an origin.

Example 2. The endoscope system according to Example 1, wherein
the operation portion includes a gas-liquid feeding button, and
the suction button is disposed on a side opposite the angle knob of the operation portion with respect to a line connecting the suction cylinder and the gas-liquid feeding button.

Example 3. The endoscope system according to Example 2, wherein the suction button is disposed closer to a proximal end side of the operation portion than the gas-liquid feeding button.

Example 4. The endoscope system according to Example 2, wherein
the operation portion includes a switch on a proximal end side of the suction cylinder, and
the suction button is disposed between the gas-liquid feeding button and the switch in a direction along a longitudinal axis of the operation portion.

Example 5. The endoscope system according to Example 2, wherein the suction button is disposed at a position separated from the suction cylinder by the predetermined distance in a direction orthogonal to a longitudinal axis of the operation portion.

Example 6. The endoscope system according to Example 2, wherein the suction button is disposed such that a first axial direction in which the suction button slides when a pressing operation is performed is tilted on the side opposite the angle knob at a predetermined angle relative to a second axial direction in which the gas-liquid feeding button slides when a pressing operation is performed.

Example 7. The endoscope system according to Example 6, wherein the predetermined angle is equal to or smaller than 60°.

Example 8. The endoscope system according to Example 2, wherein
the suction button protrudes from a top surface of the operation portion by a first height when not operated,
the gas-liquid feeding button protrudes from the top surface of the operation portion by a second height when not operated, and
the first height is higher than the second height.

Example 9. The endoscope system according to Example 2, wherein the suction button unit includes a fixation portion that is inserted into the suction cylinder, and a fixation member that is provided at the fixation portion and engages with the suction cylinder in an airtight manner.

Example 10. The endoscope system according to Example 9, wherein the fixation member includes an engagement portion, and the suction cylinder includes an engagement counterpart portion that engages with the engagement portion to prevent rotation of the suction button unit relative to the operation portion.

Example 11. A suction unit mounted on an operation portion of an endoscope, comprising:

a suction button; and a fixation portion that is inserted into a suction cylinder of the endoscope, wherein the suction button is disposed such that an axial direction in which the suction button slides when a pressing operation is performed is tilted at a predetermined angle relative to a longitudinal axis of the fixation portion.

Example 12. The suction unit according to Example 11, wherein the predetermined angle is equal to or smaller than 60°.

Example 13. The suction unit according to Example 11, comprising a suction button unit including the suction cylinder, wherein the suction button is provided at a piston member that slides inside the suction cylinder, and the fixation portion is provided at the suction button unit.

What is claimed is:

1. A suction unit for use with an endoscope, comprising:
a suction button movable along a first axis;
an attachment provided around the endoscope insertable protrusion; and
an endoscope insertable protrusion extending along a second axis,
wherein the second axis is tilted relative to the first axis, and
wherein the attachment includes a rib on an inner surface thereof.

2. The suction unit according to claim 1, wherein an angle at which the second axis is tilted relative to the first axis is equal to or smaller than 60°.

3. The suction unit according to claim 1, wherein the suction button includes a first suction channel, and
wherein the suction unit further comprises a first suction tube having a second suction channel in fluid communication with the first suction channel of the suction button.

4. The suction unit according to claim 3, further comprising a body member having a third suction channel in fluid communication with the first suction channel of the suction button.

5. The suction unit according to claim 4, wherein the suction button extends from a first surface of the body member,
wherein the endoscope insertable protrusion extends from a second surface of the body member, and
wherein the first surface is on a different side of the body member from the second surface.

6. The suction unit according to claim 4, wherein the suction button is switchable between a first state and a second state, wherein, in the first state, the first suction channel of the suction button and the third suction channel of the body member are not in fluid communication, and wherein, in the second state, the first suction channel of the suction button and the third suction channel of the body member are in fluid communication.

7. The suction unit according to claim 6, wherein, in an absence of an applied external force, the suction button is biased to be in the first state.

8. The suction unit according to claim 4, further comprising a second suction tube having a fourth suction channel in fluid communication with the third suction channel of the body member.

9. The suction unit according to claim 8, wherein the suction button includes a tube joint connecting the first suction tube, and wherein the tube joint extends opposite the second suction tube.

10. The suction unit according to claim 8, wherein the first suction tube extends along the second suction tube.

11. The suction unit according to claim 4, wherein the body member has an L shape.

12. The suction unit according to claim 4, wherein the suction button has a vent on a bottom surface of the suction button.

13. The suction unit according to claim 12, wherein the suction button is switchable between a first state and a second state, wherein, in the first state, the vent and the first suction channel of the suction button are in fluid communication, and wherein, in the second state, the third suction channel of the body member and the first suction channel of the suction button are in fluid communication.

14. The suction unit according to claim 1, wherein the endoscope insertable protrusion is configured to be inserted into an opening of a medical device to connect the suction unit to the medical device, and wherein, when the endoscope insertable protrusion is inserted into the opening, a connection between the suction unit and the medical device prevents relative movement between the suction until and the medical device.

15. The suction unit according to claim 14, wherein a surface of the endoscope insertable protrusion includes a rib, and wherein, when the endoscope insertable protrusion is inserted into the opening, the rib is configured to prevent the endoscope insertable protrusion from being removed from the opening.

16. The suction unit according to claim 1, wherein the attachment has a circular shape.

17. The suction unit according to claim 1, wherein the attachment includes a protrusion configured to prevent the suction unit from rotating.

18. An endoscope system, comprising:
an endoscope including:
an operation portion including a concavity; and
the suction unit according to claim 1,
wherein the endoscope insertable protrusion is inserted into the concavity.

19. The endoscope system according to claim 18, wherein the operation portion includes a button adjacent to the concavity, and wherein a height of the suction button from an outer surface of the operation housing is larger than a height of the button from the outer surface.

* * * * *